United States Patent
Aizawa et al.

(10) Patent No.: US 10,702,545 B2
(45) Date of Patent: Jul. 7, 2020

(54) SLOWLY DIGESTIBLE, SUSTAINED-TYPE ENERGY SUPPLYING AGENT

(71) Applicants: NIHON SHOKUHIN KAKO CO., LTD., Tokyo (JP); MORINAGA MILK INDUSTRY CO., LTD., Tokyo (JP)

(72) Inventors: Kenta Aizawa, Shizuoka (JP); Kazuki Sekikya, Shizuoka (JP); Takahisa Iizuka, Shizuoka (JP); Hiroki Takagi, Shizuoka (JP); Masayasu Takada, Shizuoka (JP); Koichi Ogawa, Shizuoka (JP); Hirofumi Sonoki, Kanagawa (JP); Akayo Ito, Kanagawa (JP); Eri Kokubo, Kanagawa (JP)

(73) Assignees: NIHON SHOKUHIN CO., LTD., Tokyo (JP); MORINAGA MILK INDUSTRY CO., LTD., Tokyo (JP)

(*) Notice: Subject to any disclaimer, the term of this patent is extended or adjusted under 35 U.S.C. 154(b) by 16 days.

(21) Appl. No.: 15/512,704

(22) PCT Filed: Sep. 18, 2015

(86) PCT No.: PCT/JP2015/076740
§ 371 (c)(1),
(2) Date: Mar. 20, 2017

(87) PCT Pub. No.: WO2016/047616
PCT Pub. Date: Mar. 31, 2016

(65) Prior Publication Data
US 2017/0304353 A1    Oct. 26, 2017

(30) Foreign Application Priority Data

Sep. 22, 2014  (JP) ................. 2014-193155

(51) Int. Cl.
| | | |
|---|---|---|
| *A61K 31/721* | (2006.01) | |
| *A61K 31/7016* | (2006.01) | |
| *A61K 31/702* | (2006.01) | |
| *A61P 3/10* | (2006.01) | |
| *A23L 33/125* | (2016.01) | |
| *A23L 2/52* | (2006.01) | |
| *C08L 5/02* | (2006.01) | |

(52) U.S. Cl.
CPC ............. *A61K 31/721* (2013.01); *A23L 2/52* (2013.01); *A23L 33/125* (2016.08); *A61K 31/702* (2013.01); *A61K 31/7016* (2013.01); *A61P 3/10* (2018.01); *C08L 5/02* (2013.01); *A23V 2002/00* (2013.01); *C08L 2203/02* (2013.01); *C08L 2205/025* (2013.01)

(58) Field of Classification Search
None
See application file for complete search history.

(56) References Cited

U.S. PATENT DOCUMENTS

| | | | | |
|---|---|---|---|---|
| 4,673,643 A | * | 6/1987 | Schwengers | ............ C12P 19/18 435/103 |
| 5,364,936 A | * | 11/1994 | Oguma | ............... C08B 37/0021 536/103 |
| 7,211,662 B2 | | 5/2007 | Backer | |
| 2004/0235789 A1 | * | 11/2004 | Day | .................... A61K 31/715 514/54 |
| 2005/0095350 A1 | | 5/2005 | Barresi | |
| 2005/0159329 A1 | | 7/2005 | Fuertes et al. | |
| 2008/0292766 A1 | | 11/2008 | Hoffman | |
| 2010/0284972 A1 | * | 11/2010 | Naeye | .................. A61K 31/733 424/93.3 |
| 2011/0020496 A1 | | 1/2011 | Shimada et al. | |
| 2013/0101697 A1 | | 4/2013 | Shimada et al. | |

FOREIGN PATENT DOCUMENTS

| | | | | |
|---|---|---|---|---|
| EP | 2248907 A1 | 11/2010 | | |
| JP | H01265867 A | 10/1989 | | |
| JP | H09107918 A | * 4/1997 | ............ A21C 13/08 | |
| JP | 2006518200 A | 8/2006 | | |
| JP | 2007135404 A | 6/2007 | | |
| JP | 2013506405 A | 2/2013 | | |
| JP | 2013087106 A | 5/2013 | | |

(Continued)

OTHER PUBLICATIONS

Bertrand, et al., Dextranase Immobilization on Epoxy CIM Disk for the Production of Isomaltooligosaccharides from Dextran, Carbohydrate Polymers, 2014, 111:707-713.
Kume, et al., Details of Meeting Presentation: Effects of Megalo-Type Isomaltosylglucose on Permeability of Rat Small Intestine, Japan Society of Nutrition and Food Science, Jun. 1, 2014.
PCT International Search Report, PCT/JP2015/076740, dated Dec. 22, 2015.
PCT English Language Translation of International Preliminary Report on Patentability, PCT/JP2015/076740, dated Mar. 28, 2017.

(Continued)

*Primary Examiner* — Dale R Miller
(74) *Attorney, Agent, or Firm* — Quarles & Brady LLP

(57) ABSTRACT

An object of the present invention is to provide a carbohydrate-derived energy supplying agent having slow digestibility and sustained digestibility functions. According to the present invention, there is provided a slowly digestible, sustained-type energy supplying agent comprising a saccharide composition which satisfies the following (A), (B), (C), and (D): (A) a percentage of $\alpha$-1,6 bonds relative to all glycosidic bonds is 60% or more; (B) a content of saccharides having a degree of polymerization of 1 and 2 relative to all saccharides is 9 mass % or less; (C) a content of saccharides having a degree of polymerization within a range of 3 to 30 relative to all saccharides is 41 mass % or more; and (D) a content of saccharides having a degree of polymerization of 31 or more relative to all saccharides is 50 mass % or less.

14 Claims, 6 Drawing Sheets

(56) References Cited

FOREIGN PATENT DOCUMENTS

| WO | 2004023891 | 3/2004 |
| WO | 2004068966 A1 | 8/2004 |
| WO | 2006054474 A1 | 5/2006 |
| WO | 2007073187 A1 | 6/2007 |
| WO | 2009113652 A1 | 9/2009 |
| WO | 2010129839 A1 | 11/2010 |
| WO | 2011071179 A1 | 6/2011 |

OTHER PUBLICATIONS

European Patent Office, Observations by a Third Party for application 15843138.7, dated Sep. 19, 2019, 34 pages.
Imahori, K. and Yamakawa T. Supervisors. Seikagaku Jiten (Dictionary of Biochemistry), 3rd edition,, pp. 928-929, 1998. With partial translation.
Sakurai, Y. (Editor). Sogo Shokuhin Jiten (Comprehensive Food Dictionary), 6th edition, pp. 566-567, 1990. With partial translation.
Shinozaki Tetsuya. Document entitled "Method for Determining Distribution of Degree of Polymerization of"Dextran 4"". Filed in opposition against Japanese patent 6453897 on Jul. 16, 2019, mailed on Aug. 9, 2019. With full translation.
Yomata, C. et al. Determination of Molecular-Weight Distribution of Dextran for Injection by Size-Exclusion Chromatography and Study for Molecular-Weight Standards. Bunseki Kagaku vol. 46, No. 12, pp. 979-985(1997). With partial translation.

* cited by examiner

SLOWLY DIGESTIBLE, SUSTAINED-TYPE ENERGY SUPPLYING AGENT

CROSS-REFERENCE TO RELATED APPLICATIONS

This application represents the national stage entry of PCT International Application No. PCT/JP2015/076760 filed Sep. 18, 2015 and claims priority to Japanese Patent Application No. 2014-193155 filed Sep. 22, 2014. The contents of these applications are hereby incorporated by reference as if set forth in their entirety herein.

TECHNICAL FIELD

The present invention relates to a slowly digestible, sustained-type energy supplying agent comprising a carbohydrate as an energy source.

BACKGROUND ART

Carbohydrates are important energy sources which are indispensable to vital activities of mammals including a human. On the other hand, energy restriction or supply, such as restriction of the intake calories for diet and other purposes or effective energy intake in sports, is performed at various scenes in the modem society. Saccharides are typical examples of the carbohydrate, and various functional saccharides have been developed in order to respond to such requests.

Under such a background, patients suffering from diabetes and potential diabetes patients are known to be rapidly increasing in association with energy intake by carbohydrates in recent years. Insulin is poorly produced and secreted in diabetes patients, so that the increase in blood sugar concentration cannot be suppressed upon intake of a carbohydrate. It is known that a continued high blood sugar concentration state gives damages to fine blood vessels and neurons which induce a number of complications. Thus, these patients need to take such foods as not to cause a sharp increase in blood sugar level. Although restricting the intake amount of a carbohydrate is effective for suppression of the blood sugar level, it is not preferable to control the increase in blood sugar level by using a method of restricting the intake amount of a carbohydrate or getting energy from a food other than the carbohydrate. Therefore, the clinical practice guidelines by the Japan Diabetes Society provide a guidepost that diabetes patients shall get 50 to 60% of intake energy from carbohydrates.

Saccharides, which are slowly digested by a digestive enzyme without sharply increasing the blood sugar level, have hitherto been developed. For example, Patent Document 1 describes a process for preparing an isomalto-oligosaccharide which is a saccharide having a low glycemic index. Patent Document 2 describes, for example, an energy supplying drink comprising a branched dextrin having a structure wherein glucose or isomalto-oligosaccharide is linked to a non-reducing terminal of the dextrin through an $\alpha$-1,6 glucosidic bond. Patent Document 3 describes a saccharide composition comprising a highly branched dextrin having a structure wherein glucose or isomalto-oligosaccharide is linked to a non-reducing terminal of the dextrin through an $\alpha$-1,6 glucosidic bond, and isomaltulose, the composition gradually raising blood sugar level. Patent Document 4 describes, for example, a sustained type energy supplying agent comprising glucosidic bonds at a percentage of 9% or more in the molecule, and also describes that effects cannot be obtained when the percentage of $\alpha$-1,3 glucosidic bonds is less than 9%.

However, a carbohydrate-derived energy supplying agent having both of slow digestibility and sustained digestibility functions and an energy supplying agent excellent in manufacture efficiency and cost have hitherto been unknown.

REFERENCE LIST

Patent Documents

Patent Document 1: JPA 2006-518200
Patent Document 2: WO 2009/113652
Patent Document 3: JAP 2013-087106
Patent Document 4: WO 2011/071179

SUMMARY OF INVENTION

An object of the present invention is to provide a carbohydrate-derived energy supplying agent having slow digestibility and sustained digestibility functions.

Now, the present inventors have found that a saccharide composition with a specific degree of polymerization, which is composed mainly of $\alpha$-1,6 bonds, is quite useful as a saccharide having slow digestibility and sustained digestibility. The present inventors have also found that the saccharide composition has the function of not greatly fluctuating the blood glucose level. The present invention is based on these findings.

Specifically, the present invention is as follows,

[1] A slowly digestible, sustained-type energy supplying agent comprising a saccharide composition which satisfies the following (A), (B), (C), and (D):

(A) a percentage of $\alpha$-1,6 bonds relative to all glycosidic bonds being 60% or more;

(B) a content of saccharides having a degree of polymerization of 1 and 2 relative to all saccharides being 9 mass % or less;

(C) a content of saccharides having a degree of polymerization within a range of 3 to 30 relative to all saccharides being 41 mass % or more; and (D) a content of saccharides having a degree of polymerization of 31 or more relative to all saccharides being 50 mass % or less.

[2] The energy supplying agent according to [1], wherein the saccharide composition comprises 3 mass % or more of saccharides having a degree of polymerization within a range of 3 to 9 relative to all saccharides.

[3] The energy supplying agent according to [1] or [2], wherein the saccharide composition comprises 10 mass % or more of saccharides having a degree of polymerization within a range of 10 to 30 relative to all saccharides.

[4] The energy supplying agent according to any one of [1] to [3], wherein the saccharide composition is a dextran degradation product or a fractionated product thereof.

[5] The energy supplying agent according to any one of [1] to [4], wherein, in the above (A), (A-1) the percentage of $\alpha$-1,6 bonds relative to all glycosidic bonds is 90% or more.

[6] The energy supplying agent according to any one of [1] to [3], wherein the saccharide composition is a dextran-producing enzyme reaction product or a fractionated product thereof.

[7] The energy supplying agent according to any one of [1] to [3] and [6], wherein, in the above (A), (A-2) the percentage of $\alpha$-1,6 bonds relative to all glycosidic bonds is 60 to 99%, and a percentage of $\alpha$-1,4 bonds relative to glycosidic bonds other than the $\alpha$-1,6 bonds is 80% or more,

[8] The energy supplying agent according to any one of [1] to [7] for supplying energy while slowing a change in blood glucose level.

[9] The energy supplying agent according to any one of [1] to [8], which is intended to be fed to a person who requires carbohydrate-derived energy but needs to slow a change in blood glucose level upon intake of the energy.

[10] A saccharide composition which satisfies the following (A), (B), (C), and (D):

(A) a percentage of α-1,6 bonds relative to all glycosidic bonds being 60% or more;

(B) a content of saccharides having a degree of polymerization of 1 and 2 relative to all saccharides being 9 mass % or less;

(C) a content of saccharides having a degree of polymerization within a range of 3 to 30 relative to all saccharides being 41 mass % or more; and (S) a content of saccharides having a degree of polymerization of 31 or more relative to all saccharides being 50 mass % or less.

[11] The saccharide composition according to [10], wherein the saccharide composition comprises 3 mass % or more of saccharides having a degree of polymerization within a range of 3 to 9 relative to all saccharides.

[12] The saccharide composition according to [10] or [11], wherein the saccharide composition comprises 10 mass % or more of saccharides having a degree of polymerization within a range of 10 to 30 relative to all saccharides,

[13] The saccharide composition according to any one of [10] to [12], which is a dextran degradation product or a fractionated product thereof

[14] The saccharide composition according to any one of [10] to [13], wherein, in the above (A), (A-1) the percentage of α-1,6 bonds relative to all glycosidic bonds is 90% or more.

[15] The saccharide composition according to any one of [10] to [12], which is a dextran-producing enzyme reaction product or a fractionated product thereof.

[16] The saccharide composition according to any one of [10] to [12] and [15], wherein, in the above (A), (A-2) the percentage of α-1,6 bonds relative to all glycosidic bonds is 60 to 99% and a percentage of α-1,4 bonds relative to glycosidic bonds other than the α-1,6 bonds is 80% or more.

[17] A food or beverage product comprising the saccharide composition according to any one of [10] to [16].

[18] The food or beverage product according to [17], comprising 6 to 25 g of the saccharide composition according to any one of [10] to [16] per 100 kcal of the food or beverage product.

[19] The food or beverage product according to [17] or [18] for slowly digestible, sustained-type energy supply.

[20] An agent for use in the treatment and prevention of a disease or a symptom for which slowing a change in blood glucose level is therapeutically or prophylactically effective, comprising the saccharide composition according to any one of [10] to [16] as an active ingredient.

[21] A method for energy supply, which comprises feeding or administering the saccharide composition according to any one of [10] to [16] or the food or beverage product according to any one of [17] to [19] to a mammal.

[22] A method for treating and/or preventing a disease or a symptom for which slowing a change in blood glucose level is therapeutically or prophylactically effective, comprising feeding or administering the saccharide composition according to any one of [10] to [16] or the food or beverage product according to any one of [1] to [19] to a mammal.

[23] Use of the saccharide composition according to any one of [10] to [16] as a slowly digestible, sustained-type energy supplying agent or a slowly digestible, sustained-type energy supplying food or beverage product.

[24] Use of the saccharide composition according to any one of [10] to [16] for the manufacture of a slowly digestible, sustained-type energy supplying agent or a slowly digestible, sustained-type energy supplying food or beverage product,

[25] Use of the saccharide composition according to any one of [10] to [16] for the manufacture of a medicament for use in the treatment and/or prevention of a disease which can be treated and/or prevented by slowing a change in blood glucose level.

The energy supplying agent, energy supplying composition and saccharide composition of the present invention are characterized in that they comprise a specific saccharide which is slowly digestible and sustainedly digested in an adequate amount. Specifically, the energy supplying agent, energy supplying composition and saccharide composition of the present invention are not quickly digested and, on the other hand, sustainedly digested in an adequate amount, when fed to mammals including a human. Thus, they can advantageously be used for energy supply during sports or at the time of disaster and further for energy supply to persons who require carbohydrate-derived energy and also require care to blood glucose.

DETAILED DESCRIPTION OF THE INVENTION

Figure 1:
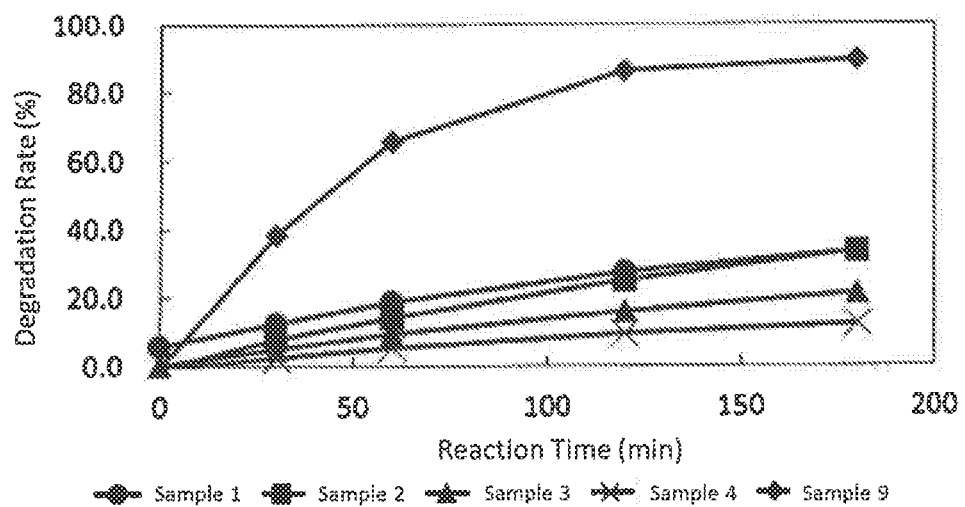
FIG. 1 shows the results of samples in an in vitro digestibility test (transition of the degradation rate (%) over 180 minutes after the beginning of a reaction).

The energy supplying agent of the present invention comprises, as an ingredient, a saccharide composition which satisfies the above (A), (B), (C), and (D) (also referred to as the "saccharide composition of the present invention" hereinafter). The energy supplying agent of the present invention, which is composed of the saccharide composition of the present invention, can be utilized as a carbohydrate-derived energy source as will be described below, and, on the other hand, has the functions of not being quickly digested and of being sustainedly digested in an adequate amount. Therefore, the present invention provides a slowly digestible, sustained-type energy supplying composition comprising, as an ingredient, the saccharide composition of the present invention (also referred to as the "energy supplying composition of the present invention" hereinafter).

The saccharide composition of the present invention is characterized in that it comprises saccharides having a high percentage of α-1,6 bonds, and specifically characterized in that it comprises saccharides wherein a percentage of α-1,6 bonds relative to all glycosidic bonds (glycosidic bonds which constitute all saccharides) is 60% or more. In order that the energy supplying agent, energy supplying composition and saccharide composition of the present invention further exert the functions of slow digestibility, sustained digestibility and low fluctuations in blood glucose level, the percentage of α-1,6 bonds in all glycosidic bonds can preferably be 65% or more, more preferably 70% or more, still more preferably 80% or more, especially preferably 90% or more. Specific examples of the saccharide composition wherein a percentage of α-1,6 bonds relative to all glycosidic bonds is 90% or more include a dextran degradation product and a fractionated product thereof which will be described later.

According to a preferred embodiment of the saccharide composition of the present invention, there is provided a saccharide composition comprising saccharides having a high percentage of α-1,6 bonds and a high percentage of α-1,4 bonds in glycosidic bonds other than the α-1,6 bonds contained at a constant level. Examples of such a saccharide composition include those wherein a percentage of α-1,6 bonds relative to all glycosidic bonds is 60 to 99% and a percentage of α-1,4 bonds relative to glycosidic bonds other than the α-1,6 bonds is 80% or more, more preferably those wherein a percentage of α-1,6 bonds relative to all glycosidic bonds is 60 to 90% and a percentage of α-1,4 bonds relative to glycosidic bonds other than the α-1,6 bonds is 80% or more, especially preferably those wherein a percentage of α-1,6 bonds relative to all glycosidic bonds is 60 to 83% and a percentage of α-1,4 bonds relative to glycosidic bonds other than the α-1,6 bonds is 80% or more. Specific examples of such a saccharide composition include a dextran-producing enzyme reaction product and a fractionated product thereof which will be described later.

The saccharide composition of the present invention may contain a saccharide having a degree of polymerization (DP) of 1 and 2, and the content thereof is 9 mass % or less relative to all saccharides (see the results of Sample 1 in the Examples). In order that the energy supplying agent and energy supplying composition of the present invention further exert the functions of slow digestibility and low fluctuation property in blood glucose level, the content of the saccharides having a degree of polymerization of 1 and 2 relative to all saccharides can preferably be 8 mass % or less, more preferably 7 mass % or less. Since the energy supplying agent and energy supplying composition of the present invention can exert the effects even if the saccharide composition of the present invention contains substantially no saccharides having a degree of polymerization of 1 and 2, the lower limit on the content of the saccharides having a degree of polymerization of 1 and 2 relative to all saccharides can be 0 mass %.

The saccharide composition of the present invention contains 41 mass % or more of saccharides having a degree of polymerization within a range of 3 to 30 relative to all saccharides. In order that the energy supplying agent and energy supplying composition of the present invention further exert the slow digestibility and sustained digestibility functions, the content of the saccharides having a degree of polymerization within a range of 3 to 3 h relative to all saccharides can preferably be 45 mass % or more, more preferably 50 mass % or more, even more preferably 60 mass % or more. According to the Examples described later, the saccharide composition of the present invention contains saccharides having a degree of polymerization within a range of 3 to 30 so that the energy supplying agent and energy supplying composition of the present invention can exert the slow digestibility and sustained digestibility functions. Therefore, the upper limit on the content of the saccharides having a degree of polymerization within a range of 3 to 30 relative to all saccharides can be 100 mass %.

The content of the saccharides having a degree of polymerization within a range of 3 to 9 relative to all saccharides in the saccharide composition of the present invention can be 3 mass % or more, preferably 10 mass % or more, more preferably 20 mass % or more, even more preferably 30 mass % or more, most preferably 40 mass % or more.

The content of the saccharides having a degree of polymerization within a range of 10 to 30 relative to all saccharides in the saccharide composition of the present invention can be 10 mass % or more, preferably 20 mass % or more, more preferably 30 mass % or more, even more preferably 40 mass % or more, most preferably 50 mass % or more.

According to the Examples described later, the saccharide composition of the present invention contains saccharides having a degree of polymerization within a range of 3 to 9 and/or saccharides having a degree of polymerization within a range of 10 to 30 so that the energy supplying agent and energy supplying composition of the present invention can exert the slow digestibility and sustained digestibility functions. Therefore, both of the upper limit on the content of the saccharides having a degree of polymerization within a range of 3 to 9 relative to all saccharides and the upper limit on the content of the saccharides having a degree of polymerization within a range of 10 to 30 relative to all saccharides can be 100 mass %. The saccharide composition of the present invention may also contain a mixture of saccharides having a degree of polymerization within a range of 3 to 9 with saccharides having a degree of polymerization within a range of 10 to 30. The content of the saccharides having a degree of polymerization within a range of 3 to 9 relative to all saccharides can be 3 mass % or more, and the content of the saccharides having a degree of polymerization within a range of 10 to 30 relative to all saccharides can be 10 mass % or more.

The saccharide composition of the present invention may contain saccharides having a degree of polymerization of 31 or more, and the content thereof is 50 mass % or less relative to all saccharides. Since saccharides having a degree of polymerization of 31 or more are not digested in an adequate amount over the time course as described in the Examples which will be given later, the content of the saccharides having a degree of polymerization of 31 or more relative to all saccharides in the saccharide composition can preferably be 40 mass % or less, more preferably 30 mass % or less, in order that the energy supplying agent and energy supplying composition of the present invention further exert the slow digestibility and sustained digestibility functions. Since the energy supplying agent and energy supplying composition of the present invention can exert the slow digestibility and sustained digestibility functions even though the saccharide composition of the present invention contains substantially no saccharides having a degree of polymerization of 31 or more, the lower limit on the content of the saccharides having a degree of polymerization of 31 or more relative to all saccharides can be 0 mass %.

The origin of, and manufacture process for, the saccharide composition of the present invention are not particularly limited so long as the composition has the properties described herein. For example, a degradation product of dextran which is an α-1,6-handed α-glucan or a fractionated product thereof can be used as the saccharide composition. In particular, a dextran degradation product or a fractionated product thereof can be obtained by appropriately degrading a dextran with an acid, an enzyme or the like to attain the desired polymerization degree formulation or by further applying fractionation treatment such as membrane fractionation, chromatographic, fractionation or precipitation fractionation, according to need, to increase the content of saccharides having a degree of polymerization within a range of 3 to 30. A commercial dextran can be used as the raw material dextran. The acid used for degradation is not particularly limited, and hydrochloric acid, sulfuric acid, oxalic acid and the like can be indicated as examples thereof. The enzyme used for degradation is also not particularly limited, and commercial dextranase and the like can be indicated as examples thereof. The fractionating method is also not particularly limited, and membrane fractionation, chromatographic fractionation, precipitation fractionation and the like can be indicated as examples thereof.

With respect to the dextran degradation conditions, those skilled in the art can set conditions under which the saccharide composition of the present invention can be obtained. For example, a dextran degradation product can be obtained by adding hydrochloric acid to 5 to 50 mass % of a dextran solution so as to arrive at 10 to 400 mM, reacting them at 60 to 90° C., for 10 to 60 hours, and thereafter subjecting the reaction product to purification such as decolorization or desalination. Also, a dextran degradation product can be obtained by adding 0.001 to 1 mg/g of substrate of dextranase, such as Dextranase L "Amano" manufactured by Amano Enzyme Inc., to 5 to 50 mass % of a dextran solution, reacting them at 30 to 80° C. for 10 to 60 hours, and thereafter subjecting the reaction product to purification such as decolorization or desalination.

A dextran-producing enzyme reaction product or a fractionated product thereof can also be used as the saccharide composition in the present invention, and, in particular, can be obtained by appropriately allowing a dextran-producing enzyme to act on a starch degradation product to attain the desired polymerization degree formulation or by applying fractionation treatment such as membrane fractionation, chromatographic fractionation or precipitation fractionation, according to need, to increase the content of saccharides having a degree of polymerization within a range of 3 to 30. That is, a dextran-producing enzyme reaction product of a starch degradation product or a fractionated product thereof can be used as the saccharide composition. The origin of the starch degradation product which used as a substrate is not particularly limited, and, for example, corn starch, potato starch, wheat starch, rice starch, sweet potato starch and tapioca starch can be used. An enzyme derived from an acetic acid bacterium can be used as the dextran-producing enzyme, and dextrin dextranase derived from *Gluconobacter oxydans* is preferably used. Since the manufacture process involving allowing a dextran-producing enzyme to act on a starch degradation product can provide the saccharide composition of the present invention more inexpensively and more easily than the above manufacture process involving dextran degradation, the manufacture process involving use of a dextran-producing enzyme is preferred from the viewpoint of industrial productivity.

Also with respect to the conditions for manufacturing the saccharide composition of the present invention using a dextran-producing enzyme, those skilled in the art can set conditions under which the saccharide composition of the present invention can be obtained. For example, the saccharide composition of the present invention can be obtained by adding 2 to 40 U/g of substrate of dextrin dextranase derived from aluconobacter oxydans to 5 to 50 mass % of a solution of partially degraded starch product, reacting them at a pH of 3 to 6 and 30 to 60° C. for 10 to 80 hours, and thereafter subjecting the reaction product to purification such as decolorization or desalination. Also, the yield of the target composition can be improved by adding α-amylase, isoamylase, pullulanase and the like during the reaction. For example, a more desired saccharide composition can be obtained by adding 0.001 to 1 mg/g of substrate of α-amylase, 20 to 2000 U/g of substrate of isoamylase, and 0.02 to 2 mg/g of substrate of pullulanase together with dextrin dextranase. In addition, the polymerization degree formulation may be adjusted by further subjecting the composition (dextran) generated by the action of the dextran-producing enzyme to degradation or fractionation treatment by the above method, thereby obtaining the saccharide composition of the present invention.

In the energy supplying agent and energy supplying composition of the present invention, a saccharide composition with the desired polymerization degree formulation obtained by allowing a dextran-producing enzyme to act on sucrose or a saccharide composition obtained by further subjecting the saccharide composition to degradation or fractionation treatment can further be used. Dextran sucrase can be used as the dextran-producing enzyme.

The saccharide composition of the present invention can use a dextran degradation product or a fractionated product thereof, or a dextran-producing enzyme reaction product or a fractionated product thereof, as described above. Accordingly, the present invention provides a process the manufacturing the energy supplying agent of the present invention, a process for manufacturing the energy supplying composition of the present invention, and a process for manufacturing the saccharide composition of the present invention, comprising the step of allowing an acid and/or an enzyme to act on a dextran for degradation to prepare a dextran degradation product and optionally subjecting the dextran degradation product to fractionation treatment or the step of allowing a dextran-producing enzyme to act on a starch degradation product to prepare an enzyme reaction product and optionally subjecting the reaction product to fractionation treatment.

When all the saccharides contained in the saccharide composition of the present invention are composed of glucose, the saccharide composition of the present invention can be expressed as a glucose polymer composition. The percentage of α-1,6 bonds in the glucose polymer composition can be expressed as "comprising saccharides wherein the percentage of α-1,6 bonds in all glucosidic bonds (glucosidic bonds which constitute all saccharides) is 60% or more." For example, a product obtained by allowing a dextran-producing enzyme to act on a starch degradation product and a fractionated product thereof can be referred to as glucose polymer compositions.

It was shown in an in vitro digestibility test in the Examples described later that the saccharide composition of the present invention is not quickly digested and is sustainedly digested in an adequate amount, and it was also shown in an in vivo digestibility test that the saccharide composition of the present invention makes a change in blood glucose slow while being digested. Accordingly, the saccharide composition of the present invention can be used for slowly digestible, sustained-type energy supply and can also be used as a slowly digestible, sustained-type energy supplying agent and a slowly digestible, sustained-type energy supplying composition, and can further be used for the manufacture of a slowly digestible, sustained-type energy supplying agent and a slowly digestible, sustained-type energy supplying composition. The saccharide composition of the present invention can also be used in a method for supplying energy to a subject which requires slowly digestible, sustained-type energy supply. The energy supplying method of the present invention can be carried out by feeding or administering the saccharide composition of the present invention to a subject including a human and a nonhuman animal.

Use of the saccharide composition of the present invention may be use in a human and a nonhuman animal, and is intended to include therapeutic use and non-therapeutic use. The term "non-therapeutic" used herein means that any activity of surgery on, treatment of, or diagnosis involving a human (namely, medical activity to a human), is not included, in particular, any method of surgery on, treatment of, or diagnosis involving a human by a doctor or a person who received a doctor's instruction is not included. Also, when the saccharide composition of the present invention is applied to a human in the present invention, it can be applied preferably to a person who requires carbohydrate-derived energy, but needs to slow a change in blood glucose level upon intake of the energy (especially, a diabetes patient) and a person who desires to or has to reduce the blood sugar level.

The energy supplying agent and energy supplying composition of the present invention are characterized in that they are slowly digestible or slowly digestible type energy supplying agent and energy supplying composition. The terms "slowly digestible" and "slowly digestible type" used herein mean "not quickly digested," and a sample can be evaluated as "not quickly digested," when its degradation rate after 180 minutes in an in vitro digestibility test using a small intestine digestive enzyme is less than 50%.

The energy supplying agent and energy supplying composition of the present invention are also characterized in that they are sustained type energy supplying agent and energy supplying composition. The term "sustained type" used herein means "sustainedly digested in an adequate amount," and a sample can be evaluated as "sustainedly digested in an adequate amount," when its degradation rate after 24 hours in an in vitro digestibility test using a small intestine digestive enzyme is 60% or more.

The in vitro digestibility test using a small intestine digestive enzyme can be conducted in accordance with the procedures described in the Examples of the present invention. In particular, the in vitro digestibility test can be conducted by dissolving a sample so as to attain a final concentration of 0.45 w/v %, adding a rat small intestine digestive enzyme so as to attain 86 U/g of substrate, and retaining the solution at 37° C. and a pH of 6.6. After stoppage of the reaction, the amount of glucose is measured by a glucose oxidase method, so that the degradation rate (digestion rate) can be calculated from the formula; degradation rate (%)=glucose mass/substrate mass×100.

The energy supplying agent and energy supplying composition of the present invention are also characterized in that those have low fluctuation property in blood glucose level. Specifically, the energy supplying agent and energy supplying composition of the present invention serve as carbohydrate-derived energy sources, and, on the other hand, have the characteristic of not greatly fluctuating the blood glucose level upon intake. Accordingly, the energy supplying agent and energy supplying composition of the present invention can be used to be fed to persons who require carbohydrate-derived energy, but require a slowed change in blood glucose level upon intake of the energy such as diabetes patients, persons called potential diabetes patients, postoperative patients, persons after gastrectomy, premature infants and persons during exercise. The phrase "persons called potential diabetes patients" used herein refers to borderline types who are not classified into normal type (persons who show a fasting blood sugar level of less than 110 mg/dl and a blood sugar level, after elapse of 2 hours in a 75-g glucose tolerance test, of less than 140 mg/dl) or diabetes type (persons who show a fasting blood sugar level of 126 mg/dl or more, a blood sugar level, after elapse of 2 hours in a sugar tolerance test, of 200 mg/dl or more, or a casual blood sugar level of 200 mg/dl or more) (diagnostic criteria by the Japan Diabetes Society).

The phrase "low fluctuation property in blood glucose level" used herein means that, when taken by mammals including a human, the change in blood glucose level is slow. In an in vivo digestibility test, in the case where the blood glucose level on administration of a sample is 90 or less when the maximum blood glucose level on administration of a control saccharide (dextrin) is defined as 100, "the change in the blood glucose level" can be evaluated as "slow."

The in vivo digestibility test can be conducted in accordance with the procedures described in the Examples of the present invention. Specifically, the in vivo digestibility test can be conducted by subjecting an overnight-fasted rat to 2-hour water deprivation, thereafter orally administering 3 g/kg of body weight of a sample to the rat, and analyzing the blood sugar levels 30, 60, 90 and 120 minutes after the administration with a simplified blood sugar measuring device. The maximum blood sugar level of a sample-administered group, when the maximum blood sugar level of a dextrin-administered group (control group) is defined as 100, can be calculated as a relative maximum blood sugar level.

The energy supplying agent and energy supplying composition of the present invention are characterized in that they are not quickly digested and sustainedly digested in an adequate amount. Accordingly, the energy supplying agent and energy supplying composition of the present invention can be utilized, for example, as energy supplying agents for infants, aged persons, medical use, sports, emergency and portable use or as agents for improving feeling of filling, through the use of their properties. They can also be utilized as feeds for rearing animals and pet foods in expectation of similar effects.

The energy supplying agent and energy supplying composition of the present invention are also characterized in that, when mammals including a human take them, the change in blood glucose level is slow. Thus, the energy supplying agent and energy supplying composition of the present invention can be used as energy supplying agents for persons who require carbohydrate-derived energy and also require care to blood glucose such as diabetes patients, persons called potential diabetes patients, perioperative patients, persons after gastrectomy, premature infants and persons during exercise. This energy supplying agent is applied to diabetes patients for the purpose of providing a carbohydrate which serves as an energy source without adversely affecting their blood sugar level, and is not intended to be administered for the prevention or treatment of diabetes.

The energy supplying agent and energy supplying composition of the present invention may comprise other ingredients within the scope in which the effects of the present invention would not be inhibited. Their form is not particularly limited, and they can be used in various forms such as a tablet, a granule, a powder, a solution, a gel and a capsule. The content of the saccharide composition of the present invention in the energy supplying agent and energy supplying composition of the present invention is not particularly limited, but is preferably 10 to 100 mass %, especially preferably 30 to 100 mass % in order to effectively exert the effects.

The energy supplying agent and energy supplying composition of the present invention may be taken as they are, and may also be incorporated in a raw material for a food or beverage product to be taken as a food or beverage product Specifically, the present invention provides a food or beverage product (including a medical food or beverage product) obtained by incorporation of the energy supplying agent or energy supplying composition of the present invention, or a saccharide composition which satisfies the above (A), (B), (C), and (D). The present invention also provides a process for manufacturing a slowly digestible and sustainedly, digestible energy supplying food or beverage product (including a medical food or beverage product), comprising incorporating, in a food or beverage product, the energy supplying agent or energy supplying composition of the present invention, or a saccharide composition which satisfies the above (A), (B), (C), and (D). In the present invention, the energy supplying agent or energy supplying composition of the present invention or the saccharide composition which satisfies the above (A), (B), (C), and (D) can be used as an additive of a food or beverage product or an agent to be incorporated therein.

The amount (in terms of solid content) of the energy supplying agent or energy supplying composition of the present invention or the above saccharide composition to be incorporated in the food or beverage product of the present invention can be 5 to 99 mass %, preferably 5 to 60 mass % based on the total mass of the food or beverage product (final product). The food or beverage product of the present invention may be manufactured either by mixing the energy supplying agent or energy supplying composition of the present invention or the above saccharide composition with a raw material for manufacturing a food or beverage product or by adding the same to a food or beverage product after completion of the main steps of manufacturing the food or beverage product.

The saccharide composition of the present invention is colorless, tasteless and odorless, and can therefore be added or incorporated into various foods without damaging their appearance, flavor and texture and widely used in all of commonly eaten food and beverage products. The food or beverage product to be provided is not particularly limited, and examples thereof include: various carbohydrates such as bread, noodles, boiled rice, and rice cakes; various Japanese-style confectionery such as rice crackers, cubic rice crackers, millet-and-rice cakes, Turkish delight (gyuhi), rice cakes, buns with a beam jam filling, bean-jam pancakes, sweet rice jelly, sweet bean paste, sweet jelly of adzuki beans, soft adzuki-bean jelly, Japanese agar jelly (kingyoku), sponge cakes called Castella, and hard candies; various Western-style confectionery such as bread, biscuits, crackers, cookies, pies, doughnuts, steamed cakes, puddings, jelly, mousse, bavarois, custard cream, cream puff, waffles, sponge cakes, chocolates, chewing gums, caramels, nougat, candies, and syrups; various ices such as ice cream, sherbet, gelato, and shaved ice; various pasty foods such as flour paste, peanut paste, margarine, and fruit paste; various beverages such as fruit juice-containing beverages, fruit juice, vegetable juice, cider, ginger ale, isotonic beverages, amino acid beverages, jelly beverages, coffee beverages, green tea, black tea, oolong tea, barley tea, milk beverages, lactic acid bacteria beverages, cocoa, beer, low-malt beer, quasi-beer, non-alcoholic beverages, beer-flavored beverages, liqueur, sho-chu-based beverages, refined sake, fruit liquor, distilled liquor, nutritional drinks, healthy beverages, and powdered drinks; fruit and vegetable processed products such as jams, marmalades, fruit and vegetable in syrup, candied fruits, and pickles; various dairy products such as cheese, yogurt, butter, condensed milk, and dry milk powder; powdered foods such as powdered soup, powdered mousse, powdered jelly, and powdered sweeteners; nutritional foods; diet foods; nutritional foods for sports; fluid diets; semi-solid fluid diets; care foods; and swallowing food. The energy supplying agent and energy supplying composition of the present invention have the functions of being not quickly digested and sustainedly digested in an adequate amount. Thus, the energy supplying agent and energy supplying composition of the present invention and the above saccharide composition are preferably added or incorporated into a raw material for a food or beverage product as a substitute for a saccharide or a starchiness in consideration of such functions. The saccharide composition of the present invention can also be used, as it is, as a meal.

The energy supplying agent and energy supplying composition of the present invention and the saccharide composition of the present invention can be provided, as they are, as food or beverage products having the energy supplying function described herein. Alternatively, the energy supplying agent and energy supplying composition of the present invention and the saccharide composition of the present invention can be incorporated in food or beverage products to be provided as food or beverage products having the energy supplying function described herein. The food or beverage product having the above energy supplying function can be a food or beverage product containing an effective amount of the saccharide composition according to the present invention for slowly digestible, sustained-type energy supply. Here, the phrase "containing an effective amount" of the saccharide composition according to the present invention used herein refers to a content of the saccharide composition according to the present invention to be taken in an amount within a range as will be described below when individual food or beverage products are eaten in a common amount. The phrase "food or beverage product" used herein encompasses health foods, functional foods, foods with health claims such as foods for specified health uses, foods with nutrient function claims and foods with function claims; and special-to-use foods such as infant foods, maternity foods and foods for sick persons. The food or beverage product having the energy supplying function according to the present invention can be provided as a food or beverage product with an indication that it is used for the energy supply described in the present invention, i.e., slowly digestible, sustained-type energy supply or energy supply related thereto.

In order that the food or beverage product of the present invention further exerts the effect of slowing a change in blood sugar level of an intaker, the saccharide composition of the present invention is preferably incorporated so that all the saccharides that constitute the food or beverage product of the present invention satisfy the above (A), (B), (C) and (D). Thus, from the viewpoint of providing the effect of slowing a change in blood sugar level of an intaker, the saccharide composition of the present invention is preferably incorporated so that the content thereof is 62 to 100 mass (solid content) % relative to the mass (solid content) of all the saccharides (including the saccharide composition of the present invention) contained in the food or beverage product of the present invention. The total amount of the saccharides contained in the food or beverage product of the present invention is not particularly limited, and can appropriately be determined according to the form of the food or beverage product and the subject for intake. The masses of the saccharide and the saccharide composition referred to herein are solid content masses, unless otherwise noted.

The food or beverage product of the present invention comprising saccharides all of which satisfy the above (A), (B), (C) and (D) can be fed to a diabetes patient, a potential diabetes patient, a person who is concerned about the blood sugar level, a person who desires to lower the blood sugar level, and a person in need of lowering the blood sugar level, for the purpose of preventing the exacerbation, progress and development of diabetes by slowing a change in blood sugar level after intake. In this case, the food or beverage product of the present invention can be provided as a meal substitute for blood sugar control use, and all or some of saccharide sources of the food or beverage product are substituted by the saccharide composition of the present invention. The subject for application can take the above food or beverage product as all or some of meals or a between-meal snack.

The food or beverage product of the present invention comprising saccharides all of which satisfy the above (A), (B), (C) and (D) can be fed to a person who is concerned about the body weight, a person who wishes slimming, a person who desires to lose the body weight, and a person in need of body weight loss, for the purpose of enhancing a feeling of filling until next meal and preventing overeating by slowing a change in blood sugar level after intake. In this case, the food or beverage product of the present invention can be provided as a meal substitute for diet, and all or some of saccharide sources of the food or beverage product are substituted by the saccharide composition of the present invention. The subject for application can take the above food or beverage product as all or some of meals or a between-meal snack.

Specific examples of the above meal substitute for blood sugar control use and meal substitute for diet include thick fluid diets such as liquid thick fluid diets, semi-solid thick fluid diets and powdery thick fluid diets; confectionery such as meal substitute cookies, meal substitute cakes and meal substitute bars; and ice cream.

The food or beverage product of the present invention comprising saccharides all of which satisfy the above (A), (B), (C) and (D) can be fed to an athlete and a person who takes exercise, for the purpose of maintaining the endurance by slowing a change in blood sugar level after intake. In this case, the food or beverage product of the present invention can be provided as a nutraceutical food for sports, and all or some of saccharide sources of food or beverage product are substituted by the saccharide composition of the present invention. The subject for application before and/or during exercise can take the above food or beverage product.

Specific examples of the nutraceutical food for sports include liquid sports drinks, semi-solid sports drinks and powdered sports drinks.

In order to provide the effect of slowing a change in blood sugar level of an intakes still further, the amount of the saccharide composition to be incorporated in the food or beverage product of the present invention can be determined for each form of the food or beverage product. For example, when the food or beverage product of the present invention is provided as a meal substitute for blood sugar control use or a meal substitute for diet, the saccharide composition of the present invention can be incorporated in the food or beverage product of the present invention so as to give 24 to 75%, preferably 31 to 65% of an energy amount based on the total energy of the food or beverage product. Also, when the food or beverage product of the present invention is provided as a nutraceutical food for sports, the saccharide composition of the present invention can be incorporated in the food or beverage product of the present invention so as to give 62 to 100% of an energy amount based on the total energy of the food or beverage product.

When the food or beverage product of the present invention is provided as a meal substitute for blood sugar control use or a meal substitute for diet, the saccharide composition of the present invention can be incorporated in the food or beverage product of the present invention so that the mass thereof is 6 to 25 g, preferably 6 to 20 g, more preferably 7 to 17 g per energy (100 kcal) of the food or beverage product. Also, when the food or beverage product of the present invention is provided as a nutraceutical food for sports, the saccharide composition of the present invention can be incorporated in the food or beverage product of the present invention so that the mass thereof is 6 to 25 g, preferably 10 to 25 g, more preferably 15 to 25 g per energy (100 kcal) of the food or beverage product.

When the food or beverage product of the present invention is provided as a meal substitute for blood sugar control use or a meal substitute for diet, the saccharide composition of the present invention can be incorporated in the food or beverage product of the present invention so that the mass thereof is 6 to 50%, preferably 7 to 26% based on the total mass of the food or beverage product. When the food or beverage product of the present invention is provided as a nutraceutical for sports, the saccharide composition of the present invention can be incorporated in the food or beverage product of the present invention so that the mass thereof is 2% to 38% based on the total mass of the food or beverage product.

The food or beverage product of the present invention can be fed to a mammal in need of slowly digestible, sustained-type energy supply, such as a human, a cow, a horse, a pig, a monkey, a dog, a cat, a mouse or a rat. The intake amount of the food or beverage product having the energy supplying function of the present invention can be determined depending on the sex, age or body weight of the subject, necessary intake calories therefor, etc and is not particularly limited so long as slowly digestible, sustained-type energy supply is attained.

The food or beverage product of the present invention is used together with other orally-ingestible functional food materials, without limitation. For example, it is used together with a resistant dextrin, a guar gum degradation product, guar gum, gum arabic, a beet fiber, a low molecular weight sodium alginate, agar, xanthan gum, gellan gum, cellulose, a polydextrose, a water-soluble soybean polysaccharide, a resistant glucan, D-psicose, a fermented black bean extract, a mulberry leaf extract, a guava leaf extract, an *Angelica keiskei* extract, a green tea extract, a black tea extract, palatinose, a highly-branched dextrin, a highly-branched cyclic dextrin, a dextrin or the like, thereby making it possible to enhance the slowly digestible, sustained-type energy supplying effect.

The food or beverage product of the present invention may be packaged either in one package or in a plurality of packages so long as it allows intake of the predetermined energy. When the food or beverage product is provided in a packaged form, it is desired that the package has a description regarding the intake amount given thereon or is provided together with a document which describes the intake amount, for allowing intake of the necessary calories to be taken for one meal. When the necessary intake calories for one meal are supplied in a plurality of packages, the packages which provide the necessary intake amount for one meal may be provided in a set, in consideration of intakers' convenience. It would be self-evident to those skilled in the art that, also when the food or beverage product with the energy supplying function according to the present invention is provided as one comprising a saccharide composition in an amount enough to supply the daily necessary intake calories for adults, the product can be provided in a similar manner as described above. When the daily necessary intake calories for one meal are supplied, a plurality of packages which provide the necessary intake amount for one meal may be provided in a set in consideration of intakers' convenience, and, additionally, the daily intake amount may be divided into two, three or four meals.

The package form for providing the saccharide composition of the present invention and the food or beverage product of the present invention comprising the saccharide composition is not particularly limited so long as a constant amount thereof is defined therein, and examples of the package form include containers in which they can be contained, such as a packaging paper, a soft bag, a paper container, a can, a bottle and a capsule.

The present invention provides a method for energy supply, which comprises feeding or administering the saccharide composition of the present invention or the food or beverage product of the present invention to a mammal.

The present invention also provides use of the saccharide composition of the present invention as a slowly digestible, sustained-type energy supplying agent or a slowly digestible, sustained-type energy supplying food or beverage product.

The present invention also provides use of the saccharide composition of the present invention for the manufacture of a slowly digestible, sustained-type energy supplying agent or a slowly digestible, sustained-type energy supplying food or beverage product.

The method for energy supply according to the present invention and the use of the saccharide composition according to the present invention can be carried out in accordance with the descriptions regarding the saccharide composition of the present invention and the use thereof.

As described above, the saccharide composition of the present invention was demonstrated not to be quickly digested and to be adequately digested in a sustained manner as indicated in an in vitro digestibility test in the Examples described later, and further was demonstrated to be digested but to slow a change in blood glucose as indicated in an in viva digestibility test. Thus, according to another aspect of the present invention, there is provided a pharmaceutical composition for treating and preventing a disease or a symptom for which slowing a change in blood glucose level is therapeutically or prophylactically effective, comprising as an active ingredient the saccharide composition of the present invention. The present invention also provides an agent for treating and preventing a disease or a symptom for which slowing a change in blood glucose level is therapeutically or prophylactically effective, comprising as an active ingredient the saccharide composition of the present invention.

The present invention also provides a method for treating and/or preventing a disease or a symptom for which slowing a change in blood glucose level is therapeutically or prophylactically effective, comprising feeding or administering a therapeutically or prophylactically effective amount of the saccharide composition of the present invention or the food or beverage product of the present invention to a mammal. Examples of the subject for treatment and prevention include persons who suffer from the above disease and persons who are at a risk of developing the above disease. The present invention further provides use of the saccharide composition according to the present invention for the manufacture of a medicament for use in the treatment and/or prevention of a disease which can be treated and/or prevented by slowing a change in blood glucose level.

Examples of the disease and symptom, for which slowing a change in blood glucose level and which are treated or prevented by the saccharide composition of the present invention, include type 1 diabetes, type 2 diabetes, pregnancy diabetes, insulin resistance and postprandial hyperglycemia.

The term "treatment" of the above disease and symptom, as used herein, encompasses prevention of the exacerbation and progress of the disease and symptom and improvement of disease and symptom. The term "prevention" of the above disease and symptom, as used herein, means administration of the active ingredient according to the present invention, for example, to a patient who has not developed the disease or a patient who develops the disease but has no subjective symptom, and encompasses reduction in risk of developing the disease or symptom.

The treating and preventing agent of the present invention and the treating and preventing composition of the present invention can be provided in a form such as medical products, quasi drugs, food or beverage products or feeds, and can be carried out in accordance with the following description. Also, the treatment method and prevention method according to the present invention and the uses according to the present invention can be carried out in accordance with the following description.

The saccharide composition of the present invention as an active ingredient can be orally administered to a human and a non-human animal. Examples of the oral agent include a granule, a powder, a tablet, a pill, a capsule agent and a syrup agent. These preparations can be made by using a pharmacologically acceptable carrier in accordance with a technique commonly used in the art. Examples of the pharmacologically acceptable carrier include an excipient, a binder, a diluent, an additive, a perfume, a buffer, a thickener, a coloring agent and a stabilizer. A process for manufacturing the oral agent is not particularly limited, and any of methods that are well known in the art can be used.

The dose of the saccharide composition according to the present invention to be administered to mammals including a human for the purpose of treatment and/or prevention of a disease or a symptom for which slowing a change in blood glucose level is therapeutically or prophylactically effective is not particularly limited so long as the effect of slowing a change in blood sugar level of the subject for administration is obtained. The saccharide composition of the present invention can be administered, for example, in a daily dose of 12 to 375 g, preferably 62 to 325 g per adult all at once or in several times, although the amount varies depending, for example, on the symptom, age or body weight.

According to the present invention, there are also provided the following inventions.

[101] A slowly digestible, sustained-type energy supplying agent comprising a saccharide composition which satisfies the following (A), (B), (C), and (D):

(A) a percentage of α-1,6 bonds relative to all glycosidic bonds being 60% or more;

(B) a content of saccharides having a degree of polymerization of 1 and 2 relative to all saccharides being 9 mass % or less;

(C) a content of saccharides having a degree of polymerization within a range of 3 to 30 relative to all saccharides being 41 mass % or more; and (D) a content of saccharides having a degree of polymerization of 31 or more relative to all saccharides being 50 mass % or less.

[102] The energy supplying agent according to [101], wherein the saccharide composition comprises 3 mass % or more of saccharides having a degree of polymerization within a range of 3 to 9 relative to all saccharides.

[103] The energy supplying agent according to [101] or [102], wherein the saccharide composition comprises 10 mass % or more of saccharides having a degree of polymerization within a range of 10 to 30 relative to all saccharides.

[104] The energy supplying agent according to any one of [101] to [103], wherein the saccharide composition is a dextran degradation product or a fractionated product thereof.

[105] The energy supplying agent according to any one of [101] to [103], wherein the saccharide composition is a product obtained by allowing a dextran-producing enzyme to act on a starch degradation product or a fractionated product thereof.

The energy supplying agent according to any one of [101] to [105], which is intended to be fed to a person who requires carbohydrate-derived energy but needs to slow a change in blood glucose level upon intake of the energy.

A food, or beverage product obtained by incorporating the energy supplying agent according to any one of [101] to [106].

A slowly digestible, sustained-type energy supplying food or beverage product obtained by incorporating a saccharide composition (provided that a content of saccharides having a degree of polymerization of 1 and 2 relative to all saccharides is 9 mass % or less, and that a content of saccharides having a degree of polymerization of 31 or more relative to all saccharides is 50 mass % or less) as the whole or a part of a carbohydrate raw material, the saccharide composition comprising a dextran degradation product or a fractionated product thereof, or a product obtained by allowing a dextran-producing enzyme to act on a starch degradation product or a fractionated product thereof.

EXAMPLES

Hereinafter, the present invention will be described in detail by way of examples, but is not limited thereto. The content proportions of saccharides, when referred to herein, mean proportions defined based on the mass of the solid component. DP designates a degree of polymerization, unless otherwise noted.

1. Preparation of Samples and Saccharide Composition Analysis Preparation of Sample 1

Dextran 70 (manufactured by Meito Sangyo Co., Ltd.) was dissolved in water so as to arrive at 25 mass %; hydrochloric acid was added so as to arrive at 45 mM; and they were reacted at 80° C. The disappearance of DP31 or more was confirmed by HPLC, and the reaction product was neutralized with sodium hydroxide. The neutralized product was purified by a conventional method, thereby obtaining a dextran degradation product (Sample 1) comprising DP1-30 as a main ingredient.

Preparation of Sample 2

The temperature of a 20 mass % aqueous solution of Sample 1 was adjusted to 50° C., and ethanol was slowly added to the solution with stirring so as to arrive at 70 v/v %, After retention at 4° C. for 3 hours, the supernatant and precipitate were recovered, and it was confirmed by HPLC that the supernatant fraction did not contain DP10 or more. The precipitate was dissolved in water again, and similar operations were repeated until an adequate amount of the supernatant fraction was obtained. The resultant supernatant fraction was recovered and subjected to gel filtration chromatography to recover and then concentrate a fraction containing DP3-9 eluted therein, thereby obtaining a dextran degradation product (Sample 2) comprising DP3-9 as a main ingredient.

Preparation of Sample 3

Sample 1 was subjected to gel filtration chromatography to recover and then concentrate a fraction containing DP10-30 eluted therein, thereby obtaining a dextran degradation product (Sample 3) comprising DP10-30 as a main ingredient, Preparation of Sample 4

Dextran 70 (manufactured by Meito Sangyo Co., Ltd.) was dissolved in water so as to arrive at 10 mass %; dextranase (Dextranase L "Amano," manufactured by Amano Enzyme Inc.) was added in an amount of 0.04 mg/g of substrate; and they were reacted at pH 6 and 60° C. After confirmation of the disappearance of saccharides having a DP more than DP150 by HPLC, the reaction was stopped by boiling deactivation, thereby obtaining a dextran degradation product.

The temperature of a 20 mass % aqueous solution of the resultant dextran degradation product was adjusted to 50° C., and ethanol was slowly added to the solution with stirring so as to arrive at 55 v/v %. After retention at 4° C. for 3 hours, the precipitate was recovered. The precipitate was dissolved in water again, and similar operations were repeated. The saccharide composition of the precipitate was analyzed by HPLC, and the operations were terminated at the time when the disappearance of DP30 or less was confirmed, thereby obtaining a dextran degradation product (Sample 4) comprising DP31-150 as a main ingredient.

Preparation of Sample 5

A partially degraded starch product (Pinedex #1, manufactured by Matsutani Chemical Industry Co., Ltd.) was dissolved in water so as to arrive at 30 mass %; *Gluconobacter oxydans*-derived dextrin dextranase, α-amylase (Kleistase L-1, manufactured by Amano Enzyme Inc.), *Myroides odoratus*-derived isoamylase and pullulanase (Pullulanase "Amano" 3, manufactured by Amano Enzyme Inc.) were added to the solution in amounts of 7 U/g of substrate, 0.01 mg/g of substrate, 200 U/g of substrate and 0.2 mg/g of substrate, respectively; and they were reacted at pH 5 and 53° C. for 72 hours, and then the reaction product was purified by a conventional method. Sample 5 was obtained through the above operations.

Preparation of Sample 6

Sample 5 was subjected to gel filtration chromatography to recover and then concentrate fractions having a DP other than DP1 and DP2, thereby obtaining Sample 6 in which DP1 and DP2 had been removed from Sample 5.

Preparation of Sample 7

A 30% (w/w) liquefied DE 6.5 corn starch solution was adjusted to have a temperature of 53° C. and a pH of 6.0; a cyclodextrin-producing enzyme of *Paenibacilius* sp., iso-amylase of *Myroides odaratus*, Pullulanase "Amano" 3 and α-glucosidase of *Aspergillus niger* were added thereto in amounts of 2 U/g of substrate, 200 U/g of substrate, 0.2 mg/g, of substrate and 2.5 U/g of substrate, respectively, for saccharification for 48 hours. This was warmed to 80° C., and Kleistase L1 was added thereto in an amount of 0.05 mg/g of substrate and allowed to act until the disappearance of an iodine reaction. This was purified and concentrated by a conventional method, and then subjected to gel filtration chromatography to recover and then concentrate fractions having a DP other than DP1 and DP2, thereby obtaining Sample 7.

Preparation of Sample 8

A branched oligosaccharide (Biotose #50, manufactured by NIHON SHOKUHIN KAKO CO., LTD.) was subjected to gel filtration chromatography to recover and then concentrate fractions having a DP other than DP1, thereby obtaining Sample 8.

Preparation of Sample 9

A dextrin (Pinedex #2, manufactured by Matsutani Chemical Industry Co., Ltd.) was used as Sample 9.

Analysis Technique

The saccharide composition was calculated using HPLC. The glycosidic bond composition was calculated from the peak area in $^1$HNMR. NMR was measured by dissolving the samples in deuterated water. The saccharide composition analysis results and α-1,6 bond percentage analysis results of the respective samples are as indicated in Table 1 and Table 2, respectively.

The HPLC conditions were as follows.
Column: MCI GEL CK02AS (20×250 mm, manufactured by Mitsubishi Chemical Corporation)
Column temperature: 80° C.
Flow rate: 0.7 ml/min.
Eluate: purified water

TABLE 1

Saccharide compostion analysis results of samples (mass %)

| Sample Name | DP1 | DP2 | DP3-9 | DP10-30 | DP31 or more |
|---|---|---|---|---|---|
| Sample 1 (dextran degradation product•DP1-30) | 5.0 | 4.2 | 36.7 | 54.1 | 0 |
| Sample 2 (dextran degradation product•DP 3-9) | 0 | 0 | 100 | 0 | 0 |
| Sample 3 (dextran degradation product•DP10-30) | 0 | 0 | 3.1 | 96.9 | 0 |
| Sample 4 (dextran degradation product•DP31-150) | 0 | 0 | 0 | 0 | 100 |
| Sample 5 (enzyme-synthesized saccharide•unfractionated) | 2.4 | 3.8 | 31.5 | 39.8 | 22.5 |
| Sample 6 (enzyme-synthesized saccharide•DP1-2 cut) | 0 | 0 | 16.7 | 51.1 | 32.2 |
| Sample 7 (branched oligosaccharide•DP1-2 cut) | 0 | 0.3 | 68.9 | 30.8 | 0 |
| Sample 8 (branched oligosaccharide•DP1 cut) | 0.6 | 33.2 | 66.1 | 0.1 | 0 |
| Sample 9 (dextrin) | 0.4 | 2.2 | 30.4 | 16.9 | 50.1 |

TABLE 2

Alpha (α)-1,6 bond percentages of samples (%)

| Sample Name | Alpha (α)-1,6 bond percentage |
|---|---|
| Sample 1 (dextran degradation product•DP1-30) | 96.9 |
| Sample 2 (dextran degradation product•DP 3-9) | 98.2 |
| Sample 3 (dextran degradation product•DP10-30) | 98.2 |
| Sample 4 (dextran degradation product•DP31-150) | 94.3 |
| Sample 5 (enzyme-synthesized saccharide•unfractionated) | 77.0 |
| Sample 6 (enzyme-synthesized saccharide•DP1-2 cut) | 77.9 |
| Sample 7 (branched oligosaccharide•DP1-2 cut) | 44.0 |
| Sample 8 (branched oligosaceharide•DP1 cut) | 72.0 |
| Sample 9 (dextrin) | 4.3 |

As a result of reviews on the percentage (%) of glycosidic bonds other than the α-1,6 bonds, it was confirmed that α-1,4 bonds occupied 80% or more of the glycosidic bonds other than the α-1,6 bonds in Samples 5 and 6 (data not shown).

2. Method for Measuring Activities of Various Enzymes

Dextrin Dextranase

To 0.5 ml of an enzyme solution diluted with purified water, 0.5 ml of 2 w/v % maltotetraose dissolved in a 50 mM sodium acetate buffer (pH 4.2) was added, and the solution was retained at 35° C. The reaction solutions were collected in an amount of 0.5 ml 5 and 60 minutes after the reaction started, and boiled to stop the reaction. This solution was subjected to HPLC to measure the amount of maltotoriose produced. One (1) U of enzyme activity was defined as the amount of the enzyme producing 1 μmol of maltotoriose for 1 minute.

The HPLC conditions were as follows.
Column: Ultron PS-80N.L (8.0×500 mm, manufactured by Shinwa Chemical Industries Ltd.), two columns connected Column temperature: 80° C.
Flow rate: 0.6 ml/min.
Eluate: purified water Isoamylase The following reaction was performed. To 100 µl of a 50 mM sodium acetate buffer (pH 6.0) containing 20 mM calcium chloride, 350 µl of 5 mg/ml waxy corn starch (manufactured by NIHON SHOKUHIN KAKO CO., LTD.) was added, and the solution was retained at 45° C. for 5 minutes. To the solution, 100 µl of an enzyme solution appropriately diluted with the same buffer was added, and then the solution was retained at 45° C. for 15 minutes. To this solution, 500 µl of an iodine solution for deactivation of the reaction (a mixture of 2 ml of a solution comprising 6.35 mg/ml iodine and 83 mg/ml potassium iodide with 8 ml of 0.1 N hydrochloric acid) was added to stop the reaction. This reaction stopping solution was retained at room temperature for 15 minutes, and 10 ml of pure water was added thereto. The absorbency at 610 nm of the solution was then measured. One (1) U of enzyme activity was defined as the amount of the enzyme increasing the absorbency at 610 nm by 0.01 under the conditions for the above method for measuring the isoamylase activity.

Cyclodextrin-Producing Enzyme

The following enzyme reaction was performed. To 0.9 ml of 1% soluble starch (NACALAI TESQUE, INC.) dissolved in a 50 mM potassium phosphate buffer (pH 6.0), 0.1 ml of an enzyme solution appropriately diluted with water was added, and the solution was retained at 40° C. for 10 minutes. To this solution. 2.5 ml of an aqueous solution of 40 mM sodium hydroxide was added to stop the reaction. The produced β-cyclodextrin was measured by a phenolphthalein method. Specifically, 0.3 ml of a solution comprising 0.1 mg/ml phenolphthalein and 2.5 mM sodium carbonate was added to the above solution, and, after stirring, the absorbency at 550 nm was measured. The amount of the produced β-cyclodextrin was obtained based on the standard curve for β-cyclodextrin created in a range of 0 to 0.1 mg/ml. One unit of cyclodextrin-producing enzyme was defined as the amount of the enzyme necessary to produce 1 mg of β-cyclodextrin for 1 minute under the above conditions.

Alpha (α) Glucosidase

The following enzyme reaction was performed. To 80 µl of 0.25% maltose dissolved in a 50 mM sodium acetate buffer (pH 4.2), 20 µl of an enzyme solution appropriately diluted with a 10 mM sodium acetate buffer (pH 4.2) containing 0.05% Triton X-100 was added, and the solution was retained at 37° C. for 10 minutes. At 10 minutes of the reaction, 50 µl of the reaction solution was extracted, and mixed with 100 µl of a 2M tris-hydrochloric acid buffer (pH 7.0) to stop the reaction. After addition of 40 µl of Glucose CII-Test Wako (manufactured by Wako Pure Chemical Industries, Ltd.) to this solution, the solution was retained at room temperature for 1 hour for color development, and the absorbency at 490 nm was measured. The amount of the produced glucose was calculated based on the standard curve for glucose created in a range of 0 to 0.01%. One unit of α-glucosidase was defined as the amount of the enzyme necessary to hydrolyze 1 µmol of maltose for 1 minute under the above conditions.

3. Digestibility Test and Consideration

In vitro Digestibility Test Method

After suspension of 2 g of a rat small intestine acetone powder (manufactured by Sigma-Aldrich Co. LLC) in 20 ml of a 45 mM sodium maleate buffer (pH 6.6), the suspension was centrifuged (19000 g, 10 minutes) to recover the supernatant. The activity of the resultant solution was measured, and the solution was used as an enzyme solution in the following in vitro digestibility test.

The activity of the rat small intestine digestive enzyme was measured as maltase activity. Forty (40)µl of a 0.1 M sodium acetate buffer (pH 6.0) was added to 15 µl of an enzyme solution appropriately diluted with pure water, and the solution was retained at 37° C. To this solution, 45 µl of a 2 w/v % maltose solution was added to initiate a reaction. After 10 minutes, 200 µl of a 2 M Tris-HCl buffer (pH 7) was added to the solution to stop the reaction, and 80 µl of Glucose C-II Test Wako (manufactured by Wako Pure Chemical Industries, Ltd.) was added. The solution was retained at 37° C. for 30 minutes for color development. A490 was measured, and the amount of free glucose was calculated based on the standard curve for glucose. The standard curve for glucose was created by adding a 2 M Tris-HCl buffer (pH 7) and a color developing reagent to 100 µl of an aqueous solution of 0 to 0.01 w/v % glucose in a similar manner as described above. One (1) U of enzyme activity was defined as the amount of the enzyme producing 2 µmol of glucose for 1 minute under the above conditions.

A sample was dissolved in a 45 mM sodium maleate buffer (pH 6.6) so as to arrive at a final concentration of 0.45 w/v %; an enzyme solution prepared by the above technique was added so as to arrive at 86 U/g of substrate; and the solution was retained at 37° C. Twenty (20)µl of the reaction solution was mixed with 200 µl of a 2 M Tris-HCl buffer to stop the reaction. Sampling was appropriately performed. The amount of glucose in the sampled solution was measured using Glucose C-II Test Wako (manufactured by Wako Pure Chemical Industries, Ltd.) by a glucose oxidase method. The degradation rate was defined as glucose mass/substrate mass×100.

In Vivo Digestibility Test Method

Eight (8) to 11 week-old SD rats (male) were fasted overnight, and analogous individuals were sorted out based on the fasting body weight and blood sugar level. After water deprivation of the sorted individuals (n=5) for 2 hours, the respective samples were orally administered thereto, in an amount of 3 g/kg of body weight, with a feeding needle. The blood sugar levels 30, 60, 90 and 120 minutes after the administration were analyzed by a simplified blood sugar measuring device. A digestible saccharide dextrin (DE=14, manufactured by Matsutani Chemical Industry Co., Ltd. and referred to as the "control saccharide" or "control saccharide (dextrin-administered group)" in the specification and drawings) was used as a control.

In Vitro Digestibility Test on Dextran Degradation Product

Figure 2:
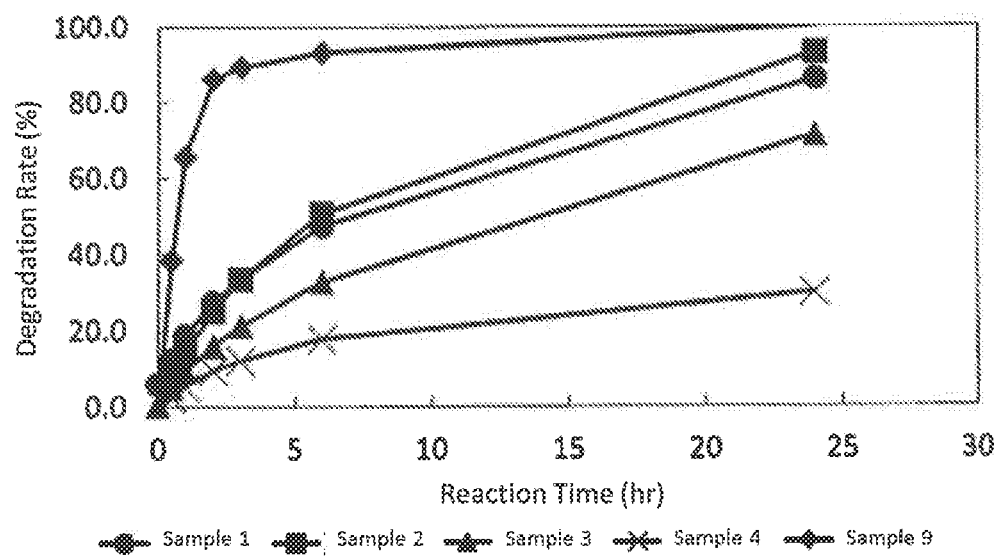
FIG. 2 shows the results of samples in the in vitro digestibility test (transition of the degradation rate (%) over 24 hours after the beginning of the reaction).

An in vitro digestibility test was conducted on dextran degradation products (Samples 1 to 4) having various degrees of polymerization and a dextrin (Sample 9). The results over 180 minutes after the reaction started are shown in FIG. 1, and the results over 24 hours after the reaction started are shown in FIG. 2. When the degradation rates over 180 minutes after the reaction started are viewed, Sample 9 was degraded at a level up to about 90%, whereas all of Samples 1 to 4 were degraded at a level of 35% or less (results after 180 minutes: 33.5% for Sample 1, 33.5% for Sample 2, 21.3% for Sample 3, and 12.2% for Sample 4). When the reaction was extended to 24 hours, Samples 1 to 3 were degraded at a level of 70% or more, whereas the degradation rate of Sample 4 was still about 30% (results after 24 hours: 86.1% for Sample 1, 93.1% for Sample 2, and 71.3% for Sample 3). The results demonstrated that saccharides of DP1-30 composed mainly of α-1,6 bonds are not quickly digested and are adequately digested in a sustained manner, as compared with the dextrin (Sample 9) composed mainly of α-1,4 bonds. Also, from the results of Sample 4 that the degradation speed is more greatly reduced for saccharides of DP31 or more, it was clarified that the sample would not be digested in an adequate amount. While the saccharides of Sample 4 do not include any saccharide having a degree of polymerization exceeding 150, it was confirmed, through the in vitro digestibility test, that the saccharides having a degree of polymerization exceeding 150 also would not be digested in an adequate amount, as with Sample 4 (data not shown).

Figure 3:
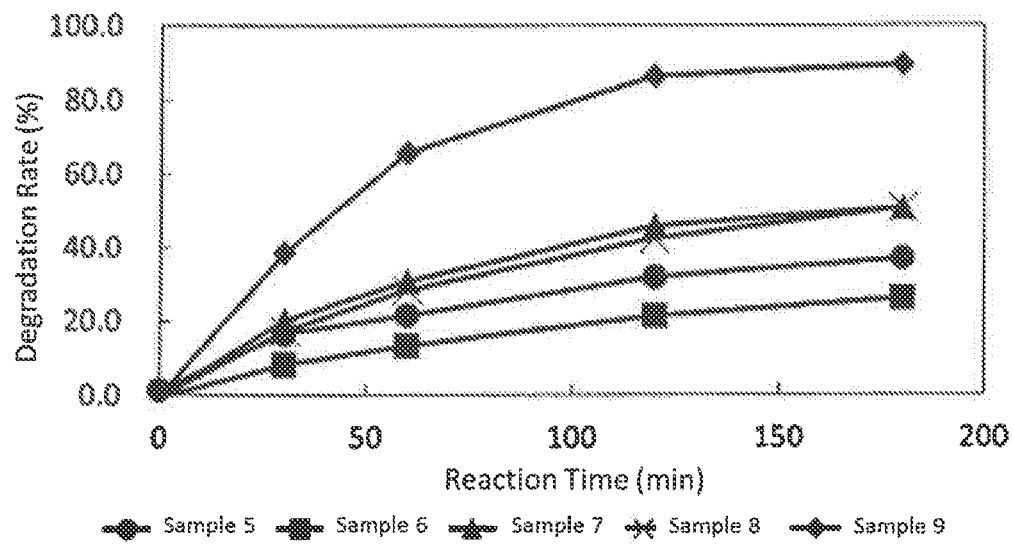
FIG. 3 shows the results of samples in the in vitro digestibility test (transition of the degradation rate (%) over 180 minutes after the beginning of the reaction).
Figure 4:
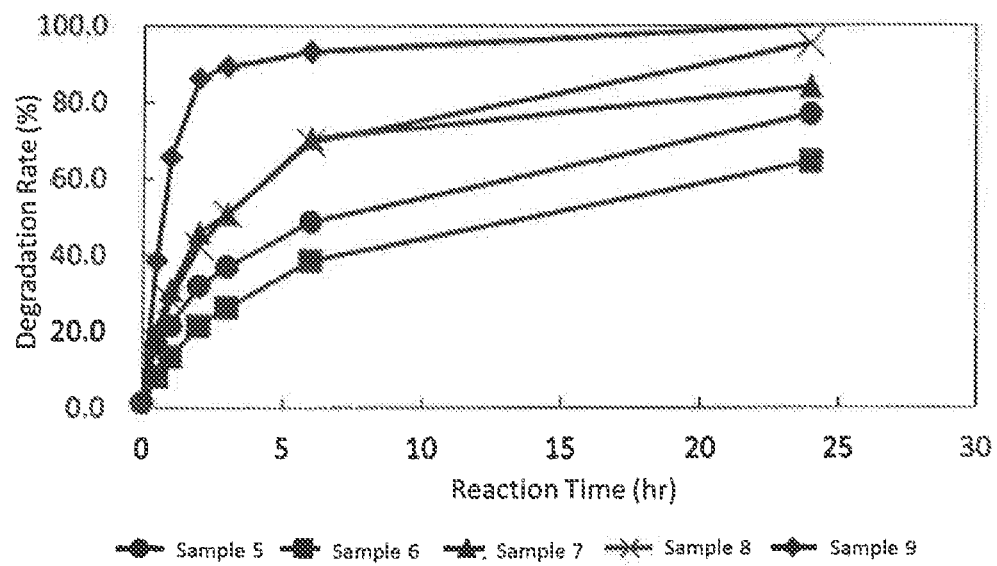
FIG. 4 shows the results of samples in the in vitro digestibility test (transition of the degradation rate (%) over 24 hours after the beginning of the reaction).
Figure 5:
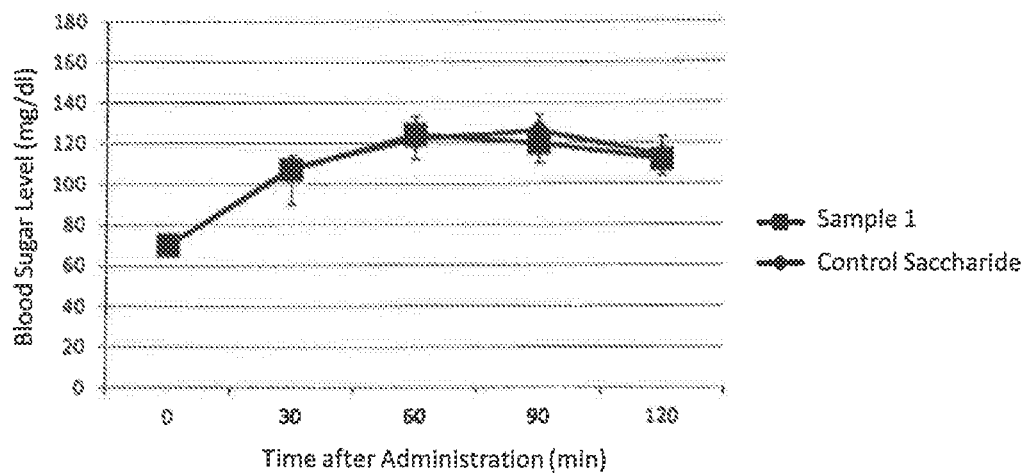
FIG. 5 shows the results of Sample 1 in an in vivo digestibility test (transition of the blood sugar level (mg/dl) over 120 minutes after administration) in comparison with the results of a control saccharide (dextrin-administered group).
Figure 6:
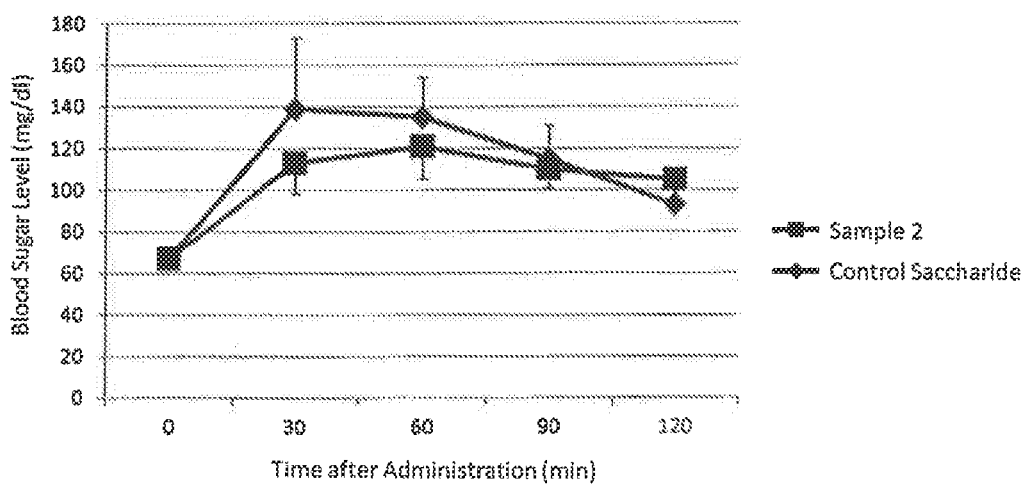
FIG. 6 shows the results of Sample 2 in the in vivo digestibility test (transition of the blood sugar level (mg/dl) over 120 minutes alter the administration) in comparison with the results of the control saccharide (dextrin-administered group).
Figure 7:
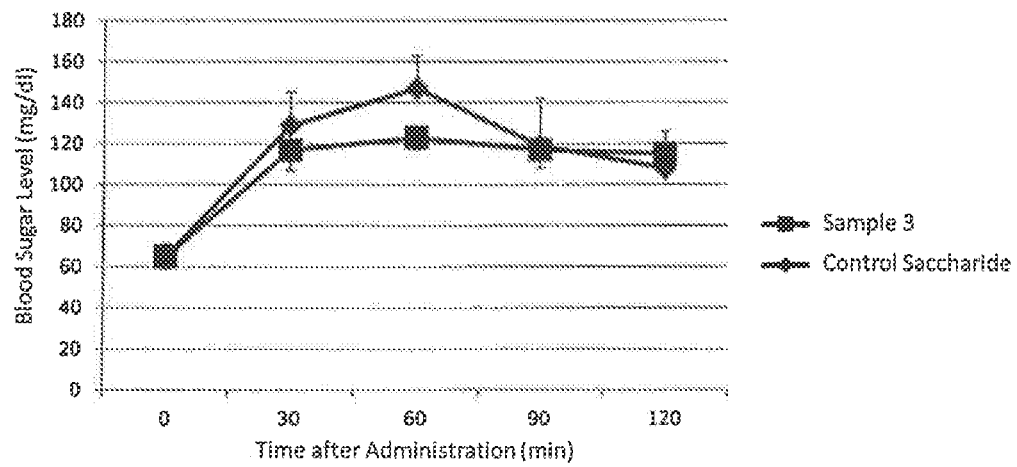
FIG. 7 shows the results of Sample 3 in the in vivo digestibility test (transition of the blood sugar level (mg/dl) over 120 minutes after the administration) in comparison with the results of the control saccharide (dextrin-administered group).
Figure 8:
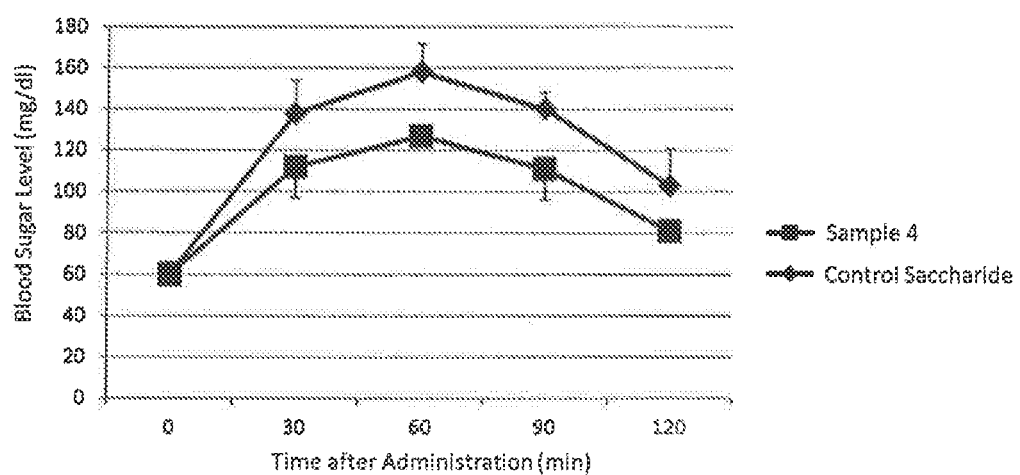
FIG. 8 shows the results of Sample 4 in the in vivo digestibility test (transition of the blood sugar level (mg/dl) over 120 minutes after the administration) in comparison with the results of the control saccharide (dextrin-administered group).
Figure 9:
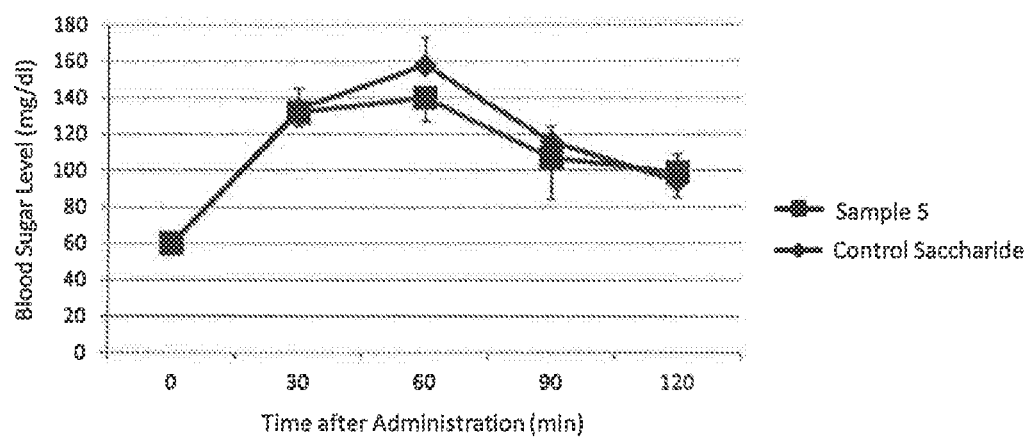
FIG. 9 shows the results of Sample 5 in the in vivo digestibility test (transition of the blood sugar level (mg/dl) over 120 minutes after the administration) in comparison with the results of the control saccharide (dextrin-administered group).
Figure 10:
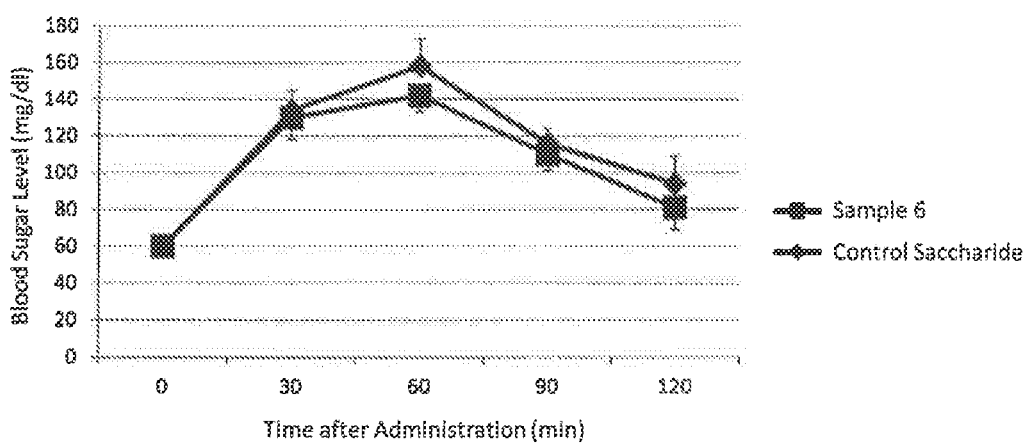
FIG. 10 shows the results of Sample 6 in the in vivo digestibility test (transition of the blood sugar level (mg/dl) over 120 minutes after the administration) in comparison with the results of the control saccharide (dextrin-administered group).
Figure 11:
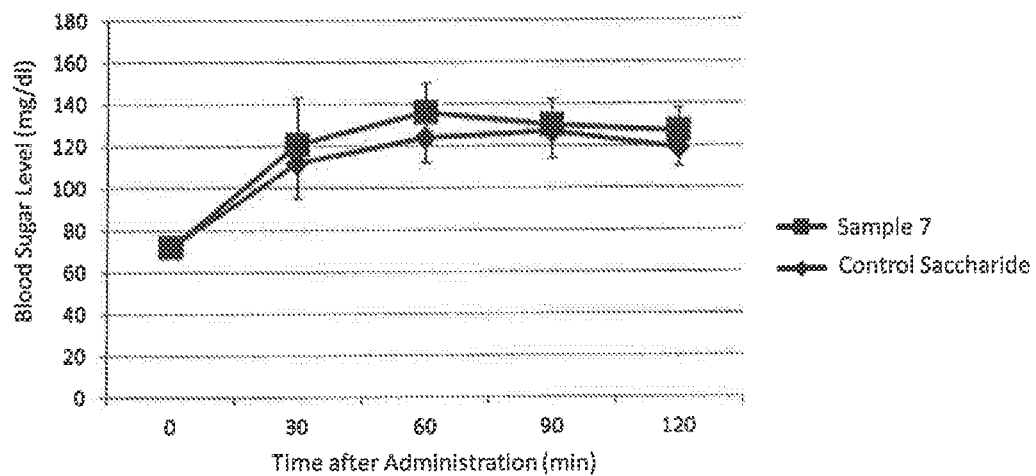
FIG. 11 shows the results of Sample 7 in the in vivo digestibility test (transition of the blood sugar level (mg/dl) over 120 minutes after the administration) in comparison with the results of the control saccharide (dextrin-administered group).
Figure 12:
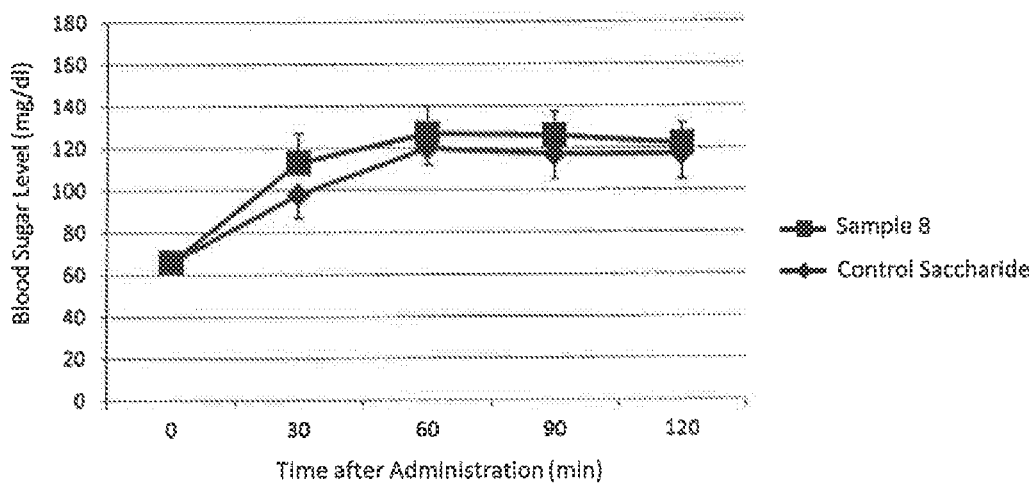
FIG. 12 shows the results of Sample 8 in the in vivo digestibility test (transition of the blood sugar level (mg/dl) over 120 minutes after the administration) in comparison with the results of the control saccharide (dextrin-administered group).

In Vitro Digestibility Test on α-1,6-Bonded Saccharide Manufactured from Starch as a Raw Material An in vitro digestibility test was conducted on various saccharides (Samples 5 to 8) having α-1,6 bonds and manufactured from starch as a raw material and a dextrin (Sample 9). The results over 180 minutes after the reaction started are shown in FIG. 3, and the results over 24 hours after the reaction started are shown in FIG. 4. When the degradation rates over 180 minutes after the reaction started are viewed, Sample 9 was degraded at a level up to about 90%, whereas the degradation rates of Samples 5 and 6 were 40% or less (results after 180 minutes: 36.9% for Sample 5 and 26.1% for Sample 6)). About Samples 7 and 8 were degraded at a level of about 50% (results after 180 minutes: 50.7% for Sample 7 and 50.7% for Sample 8). When the reaction was extended to 24 hours, all of Samples 5 to 8 were degraded at a level of 60% or more (results after 24 hours: 77.0% for Sample 5, 64.4% for Sample 6, 84.1% for Sample 7, and 95.4% for Sample 8). The results of Sample 7 demonstrated that saccharides having an α-1,6 bond percentage of less than 50% are quickly digested. Also, the results of Sample 8 demonstrated that saccharides having a sufficient α-1,6 bond percentage but a high content of DP2 are quickly digested. The results of Samples 5 and 6 demonstrated that saccharides having an α-1,6 bond percentage of 60% or more and a relatively low content of saccharides having DP1 or DP2 are not quickly digested and are adequately digested in a sustained manner, as compared with the dextrin (Sample 9) composed mainly of α-1,4 bonds.

In Vivo Digestibility Test

An in vivo digestibility test was conducted on Samples 1 to 8 and a control saccharide (dextrin-administered group). The blood sugar levels over 120 minutes after administration are shown in FIG. 5 to FIG. 12. The maximum blood sugar levels for the respective samples was calculated as the relative maximum blood sugar levels, when the maximum blood sugar level for the control saccharide (dextrin-administered group) was defined as 100. The results are as indicated in Table 3.

TABLE 3

Relative maximum blood sugar levels for samples

| | Relative maximum blood sugar level |
|---|---|
| Sample 1 (dextran degradation product•DP1-30) | 98 |
| Sample 2 (dextran degradation product•DP 3-9) | 87 |
| Sample 3 (dextran degradation product•DP10-30) | 84 |
| Sample 4 (dextran degradation product•DP31-150) | 80 |
| Sample 5 (enzyme-synthesized saccharide•unfractionated) | 88 |
| Sample 6 (enzyme-synthesized saccharide•DP1-2 cut) | 90 |
| Sample 7 (branched oligosaccharide•DP1-2 cut) | 107 |
| Sample 8 (branched oligosaccharide•DP1 cut) | 106 |

The relative maximum blood sugar level for Sample 1 was 98, which value was almost the same as the maximum blood sugar level for the control saccharide (dextrin-administered group) (the maximum blood sugar level of the Sample 1-administered group was 124, whereas that of the dextrin-administered group was 126). On the other hand, the relative maximum blood sugar levels for Sample 2 and 3 were 90 or less, which showed maximum blood sugar levels lower than that for the control saccharide (dextrin-administered group) (the maximum blood sugar level of the Sample 2-administered group was 121, whereas that of the dextrin-administered group was 139; and the maximum blood sugar level of the Sample 3-administered group was 123, whereas that of the dextrin-administered group was 147). This value was greater than the relative maximum blood sugar level (80) for Sample 4 (the maximum blood sugar level of the Sample 4-administered group was 127, whereas that of the dextrin-administered group was 158). The results of the in vivo digestibility test shown in FIG. 8 indicate that the maximum blood sugar level for Sample 4 is 80 when the maximum blood sugar level for the control saccharide (dextrin-administered group) is defined as 100, and the results of the in vitro digestibility test shown in FIG. 2 indicate that the degradation rate after 24 hours is still 30% for Sample 4. It is therefore considered that Sample 4 is not digested in an adequate amount because it comprises a fraction of resistant saccharides. On the other hand, Samples 2 and 3 provide a relative maximum blood sugar level greater than that for Sample 4, and the results of the in vitro digestibility test shown in FIG. 2 show that the degradation rates, after 24 hours, of Sample 2 and 3 are 70% or more. It was therefore indicated that Samples 2 and 3 are saccharides which are digested but slow a change in blood glucose.

Samples 5 and 6 have the same saccharide compositions as those of Samples 2 and 3, in that they are saccharide compositions wherein a percentage of α-1,6 bonds relative to all glycosidic bonds is 60% or more; a content of saccharides having a degree of polymerization of 1 and 2 relative to all saccharides is 9 mass % or less; a content of saccharides having a degree of polymerization within a range of 3 to 30 relative to all saccharides is 41 mass % or more; and a content of saccharides having a degree of polymerization of 31 or more relative to all saccharides is 50 mass % or less. It was therefore considered that the saccharides contained in Samples 5 and 6 present similar results to those of Samples 2 and 3. In fact, the relative maximum blood sugar levels for Samples 5 and 6 were 88 and 90, respectively, and the saccharides of Samples 5 and 6 presented almost equivalent results to those of the saccharides of Samples 2 and 3.

Samples 7 and 8 shown a relative maximum blood sugar level of more than 100, which showed a maximum blood suer level exceeding the maximum blood sugar level for the control saccharide (dextrin-administered group) (the maximum blood sugar level of the Sample 7-administered group was 136, whereas that of the dextrin-administered group was 127; and the maximum blood sugar level of the Sample 8-administered group was 127, whereas that of the dextrin-administered group was 120). In other words, Samples 7 and 8 were demonstrated to be saccharides having digestibility and absorbability equivalent to or higher than those of dextrin.

The invention claimed is:

1. A method for energy supply to a mammal, which comprises feeding or administering to the mammal a saccharide composition, wherein said saccharide composition is a dextran degradation product or a fractionated product thereof, or a dextran-producing enzyme reaction product or a fractionated product thereof, which satisfies the following (A), (B), (C), (D), and (E):
- (A) a percentage of α-1,6 bonds relative to all glycosidic bonds being 60% or more;
- (B) a content of saccharides having a degree of polymerization of 1 and 2 relative to all saccharides being 9 mass % or less;
- (C) a content of saccharides having a degree of polymerization within a range of 3 to 30 relative to all saccharides being 41 mass % or more;
- (D) a content of saccharides having a degree of polymerization of 31 or more relative to all saccharides being 40 mass % or less; and
- (E) a content of saccharides having a degree of polymerization within a range of 10 to 30 relative to all saccharides being 20 mass % or more, and
wherein the saccharide composition is (i) slowly digestible and (ii) has a slow change in blood glucose levels upon intake.

2. The method according to claim 1, wherein the saccharide composition comprises 3 mass % or more of saccharides having a degree of polymerization within a range of 3 to 9 relative to all saccharides.

3. The method according to claim 1, wherein the saccharide composition comprises 30 mass % or more of saccharides having a degree of polymerization within a range of 10 to 30 relative to all saccharides.

4. The method according to claim 1, wherein, in the above (A), (A-1) the percentage of α-1,6 bonds relative to all glycosidic bonds is 90% or more.

5. The method according to claim 1, wherein, in the above (A), (A-2) the percentage of α-1,6 bonds relative to all glycosidic bonds is 60 to 99%, and a percentage of α-1,4 bonds relative to glycosidic bonds other than the α-1,6 bonds is 80% or more.

6. The method according to claim 1, wherein the mammal is a human.

7. The method according to claim 6, wherein the human is a diabetic patient.

8. The method according to claim 1, wherein the saccharide composition is part of a food or beverage product.

9. A method for treating a disease or a symptom for which slowing a change in blood glucose level is therapeutically effective, comprising feeding or administering to a mammal a saccharide composition, wherein said saccharide composition is a dextran degradation product or a fractionated product thereof, or a dextran-producing enzyme reaction product or a fractionated product thereof, which satisfies the following (A), (B), (C), (D) and (E):
- (A) a percentage of α-1,6 bonds relative to all glycosidic bonds being 60% or more;
- (B) a content of saccharides having a degree of polymerization of 1 and 2 relative to all saccharides being 9 mass % or less;
- (C) a content of saccharides having a degree of polymerization within a range of 3 to 30 relative to all saccharides being 41 mass % or more;
- (D) a content of saccharides having a degree of polymerization of 31 or more relative to all saccharides being 50 mass % or less; and
- (E) a content of saccharides having a degree of polymerization within a range of 10 to 30 relative to all saccharides being 20 mass % or more, and
wherein the saccharide composition is (i) slowly digestible and (ii) has a slow change in blood glucose levels upon intake.

10. The method according to claim 9, wherein the saccharide composition comprises 3 mass % or more of saccharides having a degree of polymerization within a range of 3 to 9 relative to all saccharides.

11. The method according to claim 9, wherein the saccharide composition comprises 30 mass % or more of saccharides having a degree of polymerization within a range of 10 to 30 relative to all saccharides.

12. The method according to claim 9, wherein, in the above (A), (A-1) the percentage of α-1,6 bonds relative to all glycosidic bonds is 90% or more.

13. The method according to claim 9, wherein, in the above (A), (A-2) the percentage of α-1,6 bonds relative to all glycosidic bonds is 60 to 99%, and a percentage of α-1,4 bonds relative to glycosidic bonds other than the α-1,6 bonds is 80% or more.

14. The method according to claim 9, wherein the saccharide composition is part of a food or beverage product.

* * * * *

UNITED STATES PATENT AND TRADEMARK OFFICE
CERTIFICATE OF CORRECTION

PATENT NO. : 10,702,545 B2
APPLICATION NO. : 15/512704
DATED : July 7, 2020
INVENTOR(S) : Kenta Aizawa et al.

It is certified that error appears in the above-identified patent and that said Letters Patent is hereby corrected as shown below:

In the Specification

Column 1, Line 27, "modem" should be --modern--.

Column 1, Line 66, "comprising glucosidic" should be --comprising α1,3 glucosidic--.

Column 2, Line 14, "JAP" should be --JPA--.

Column 3, Line 19, "(S)" should be --(D)--.

Column 3, Line 43, "99%" should be --90%--.

Column 3, Line 67, "[1]" should be --[17]--.

Column 4, Line 50, "alter" should be --after--.

Column 6, Line 31, "3 to 3 h relative" should be --3 to 30 relative--.

Column 7, Line 36, "α1,6-handed" should be --α1,6-bonded--.

Column 8, Line 38, "aluconobacter" should be --Gluconobacter--.

Column 8, Line 67, "process the" should be --process for--.

Column 12, Line 25, "a beam jam" should be --bean-jam--.

Column 12, Line 51, "swallowing food" should be --swallowing foods--.

Column 14, Line 23, "of food" should be --of the food--.

Signed and Sealed this
Eighteenth Day of August, 2020

Andrei Iancu
*Director of the United States Patent and Trademark Office*

CERTIFICATE OF CORRECTION (continued)
U.S. Pat. No. 10,702,545 B2

Column 15, Line 3, "nutraceutical for" should be --nutraceutical food for--.

Column 15, Line 6, "38%" should be --88%--.

Column 16, Line 22, "viva" should be --vivo--.

Column 17, Line 66, "The energy" should be --[106] The energy--.

Column 18, Line 3, "A food," should be --[107] A food,--.

Column 18, Line 6, "A slowly" should be --[108] A slowly--.

Column 19, Line 38, "Paenibacilius" should be --Paenibacillus--.

Column 19, Line 39, "odaratus" should be --odoratus--.

Column 24, Line 53, "suer" should be --sugar--.